(12) United States Patent
Maranta et al.

(10) Patent No.: US 8,298,803 B2
(45) Date of Patent: Oct. 30, 2012

(54) POLYPEPTIDES HAVING ARABINOFURANOSIDASE ACTIVITY AND POLYNUCLEOTIDES ENCODING SAME

(75) Inventors: Michelle Maranta, Davis, CA (US); Kimberly Brown, Elk Grove, CA (US); James Langston, Sacramento, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/269,887

(22) Filed: Oct. 10, 2011

(65) Prior Publication Data
US 2012/0028334 A1    Feb. 2, 2012

Related U.S. Application Data

(62) Division of application No. 12/274,774, filed on Nov. 20, 2008, now Pat. No. 8,034,599.

(60) Provisional application No. 60/991,484, filed on Nov. 30, 2007.

(51) Int. Cl.
*C12N 9/24* (2006.01)
*C12N 1/20* (2006.01)
*C12N 15/00* (2006.01)
*C12N 5/10* (2006.01)
*C12N 5/00* (2006.01)
*C07H 21/04* (2006.01)

(52) U.S. Cl. .......... 435/200; 435/252.3; 435/320.1; 435/410; 435/419; 536/23.2

(58) Field of Classification Search .......... 435/200, 435/252.3, 320.1, 410, 419; 536/23.2
See application file for complete search history.

(56) References Cited

FOREIGN PATENT DOCUMENTS

| WO | 96/06935 A2 | 3/1996 |
|---|---|---|
| WO | 03/106654 A2 | 12/2003 |
| WO | 2006/125438 A1 | 11/2006 |
| WO | 2007/094852 A2 | 8/2007 |

OTHER PUBLICATIONS

Sorensen et al., Humicola insolens: mode of action and synergy with GH51 [alpha]-1-arabinofuranosidases on wheat arabinoxylan, 2006, Applied Microbiology and Biotechnology, 73, 850-861.
Sorensen et al., Enzymatic hydrolysis of wheat arabinoxylan by a recombinant "minimal" enzyme cocktail containing beta-xylosidase and novel endo-1, 4-beta-xylanase and alpha-(L)-arabinofuranosidase activities, Biotechnology Progress, 2007, 23, 100-107.
Database Geneseq, XP002520700, Xylanase from an environmental sample seq id 54, Apr. 22, 2004.
Filho 1996, Appl Environ Microbiol 62 (1), 168-173.
Kaji 1970, Biochim Biophys Acta 207, 456-464.
Kaji 1971, Biochim Biophys Acta 250, 367-371.
Tagawa 1969, Carbohydr Res 11, 293-301.

*Primary Examiner* — Tekchand Saidha
(74) *Attorney, Agent, or Firm* — Robert L Starnes

(57) ABSTRACT

The present invention relates to isolated polypeptides having alpha-L-arabinofuranosidase activity and isolated polynucleotides encoding the polypeptides. The invention also relates to nucleic acid constructs, vectors, and host cells comprising the polynucleotides as well as methods of producing and using the polypeptides.

13 Claims, 4 Drawing Sheets

Fig. 1A

```
865   GCCTGCAACCTCCAGCTGCTGTACCAGGGCCTGCAGGGCCAGCAGCGACTATAACAGCCTTCCGTACCGG
      P  G  L  T  M  V  G  A  R  P  G  N  G  G  N  N  Q  P  Q  T
937   CCTGGTCTGCTCACCATGGTCGGTGCCCGGCCCGGGAACGGTGGCGGTAACAACCAGCCCCAGCCCACGACG
      T  S  S  P  A  N  T  P  P  N  N  G  G  G  A  T  V  P  R  W
1009  ACCAGCAGCCCCGCCAACACCCCGCCGAACAACGGTGGCGGGGCGACCGGTTCCCTCCGGTGG
      G  Q  G  Q  Y  T  G  P  T  R  C  E  P  Y  T  C  Q  Y  S  N
1081  GGCCAGTGCGGTGGTCAGGGATATACCGGACGCGCTTGCGAGCCGCCTTATACTTGCCAGTACTCGAAT
      P  C  K  *
1153  CCTTGTAAGTAA
```

Fig. 1B

```
                    SEQUENCE LISTING

<160> NUMBER OF SEQ ID NOS: 13

<210> SEQ ID NO 1
<211> LENGTH: 1164
<212> TYPE: DNA
<213> ORGANISM: Humicola insolens

<400> SEQUENCE: 1
atgaggtcgg ttgctgcttt cctcgcggct gtgctccccg ccgtcgacgc ggcgtgcagt      60
ctcccatcca gccttagctg gacgtcgtcg ggtgctctgg cccagcccag gaatgggtgg     120
aggaacctca aggacttcac ctatgtgccg tacaacggca agcacctcgt ctacggcagc     180
tactacgacg gcaaccggta tgggtccatg aactttgggc tcttctccaa ctggaacgag     240
atggccagcg cgagccagaa cgccatgtcc aatgccgccg tcgctccgac cctcttctac     300
ttccagccca agaacatctg ggttctcgcc taccaatggg gccggactgc cttctcgtac     360
cggaccagca gcgacccgac caaccccaac ggctggtccg ccgagcagcc tctcttctcg     420
ggctccatca gcgacagctc gaccggcccc atcgaccaga ccctcatcgc cgacgacacc     480
cacatgtacc tcttcttcgc cggcgacaac ggccgcatct accgctcgcg catgccatc      540 ggcaacttcc ccagcagctt cggcagctcc tatgagacca tcatgacggg caaccgcaac     600
gacctcttcg aggccgtcca ggtgtacacc atcgacggct ccaaccccaa gcagtacctc     660
atgctcgtcg agtccatcgg ctcccgcggc cgctacttcc gctcctacgt ctccaacaac     720
ctcaacggcg cctggacccc gcacctcacc agcgagaaca accccttcgc cggccgctcc     780 aacgcccca acgccacctg gacctccgac atcagccacg gcgacctcgt ccgccttcgt     840
cctgaccaga ccttccccgt cgacgcctgc aacctccagc tgctgtacca gggcctgcag     900
ggcagcagca gcgactataa cagccttccg taccggcctg gtctgctcac catggtcggt     960
gcccggcccg ggaacggcgg cggtaacaac cagcccagc ccacgacgac cagcagcccg    1020
ccggcgaaca ccccgccccc gaacaacggc ggcggcggtg gtgcgacggt tcctcgctgg    1080
ggccagtgcg gtggtcaggg atataccggc ccgacgcgct gcgagccgcc ttatacttgc    1140
cagtactcga atccttgtaa gtaa                                           1164

<210> SEQ ID NO 2
<211> LENGTH: 387
<212> TYPE: PRT
<213> ORGANISM: Humicola insolens

<400> SEQUENCE: 2
```

```
Met Arg Ser Val Ala Ala Phe Leu Ala Ala Val Leu Pro Ala Val Asp
1               5                   10                  15
Ala Ala Cys Ser Leu Pro Ser Ser Leu Ser Trp Thr Ser Ser Gly Ala
            20                  25                  30
Leu Ala Gln Pro Arg Asn Gly Trp Arg Asn Leu Lys Asp Phe Thr Tyr
        35                  40                  45
Val Pro Tyr Asn Gly Lys His Leu Val Tyr Gly Ser Tyr Tyr Asp Gly
    50                  55                  60
Asn Arg Tyr Gly Ser Met Asn Phe Gly Leu Phe Ser Asn Trp Asn Glu
65                  70                  75                  80
Met Ala Ser Ala Ser Gln Asn Ala Met Ser Asn Ala Ala Val Ala Pro
                85                  90                  95
Thr Leu Phe Tyr Phe Gln Pro Lys Asn Ile Trp Val Leu Ala Tyr Gln
            100                 105                 110
Trp Gly Arg Thr Ala Phe Ser Tyr Arg Thr Ser Ser Asp Pro Thr Asn
        115                 120                 125
Pro Asn Gly Trp Ser Ala Glu Gln Pro Leu Phe Ser Gly Ser Ile Ser
    130                 135                 140
Asp Ser Ser Thr Gly Pro Ile Asp Gln Thr Leu Ile Ala Asp Asp Thr
145                 150                 155                 160
His Met Tyr Leu Phe Phe Ala Gly Asp Asn Gly Arg Ile Tyr Arg Ser
                165                 170                 175
Arg Met Pro Ile Gly Asn Phe Pro Ser Ser Phe Gly Ser Ser Tyr Glu
            180                 185                 190
Thr Ile Met Thr Gly Asn Arg Asn Asp Leu Phe Glu Ala Val Gln Val
        195                 200                 205
Tyr Thr Ile Asp Gly Ser Asn Pro Lys Gln Tyr Leu Met Leu Val Glu
    210                 215                 220
Ser Ile Gly Ser Arg Gly Arg Tyr Phe Arg Ser Tyr Val Ser Asn Asn
225                 230                 235                 240
Leu Asn Gly Ala Trp Thr Pro His Leu Thr Ser Glu Asn Asn Pro Phe
                245                 250                 255
Ala Gly Arg Ser Asn Ala Pro Asn Ala Thr Trp Thr Ser Asp Ile Ser
            260                 265                 270
His Gly Asp Leu Val Arg Leu Arg Pro Asp Gln Thr Phe Pro Val Asp
        275                 280                 285
Ala Cys Asn Leu Gln Leu Leu Tyr Gln Gly Leu Gln Gly Ser Ser Ser
    290                 295                 300
Asp Tyr Asn Ser Leu Pro Tyr Arg Pro Gly Leu Leu Thr Met Val Gly
305                 310                 315                 320
Ala Arg Pro Gly Asn Gly Gly Asn Asn Gln Pro Gln Pro Thr Thr
                325                 330                 335
Thr Ser Ser Pro Pro Ala Asn Thr Pro Pro Asn Asn Gly Gly Gly
            340                 345                 350
Gly Gly Ala Thr Val Pro Arg Trp Gly Gln Cys Gly Gly Gln Gly Tyr
        355                 360                 365
Thr Gly Pro Thr Arg Cys Glu Pro Pro Tyr Thr Cys Gln Tyr Ser Asn
    370                 375                 380
Pro Cys Lys
385

<210> SEQ ID NO 3
<211> LENGTH: 28
<212> TYPE: DNA
```

```
<213> ORGANISM: Humicola insolens
<220> FEATURE:
<221> NAME/KEY: misc_feature
<222> LOCATION: (17)..(17)
<223> OTHER INFORMATION: N = A, C, G, OR T
<220> FEATURE:
<221> NAME/KEY: misc_feature
<222> LOCATION: (23)..(23)
<223> OTHER INFORMATION: N = A, C, G, OR T
<220> FEATURE:
<221> NAME/KEY: misc_feature
<222> LOCATION: (26)..(26)
<223> OTHER INFORMATION: Y = C or T

<400> SEQUENCE: 3
ccaagtcgat ctgggtnctc gcntayca                                    28

<210> SEQ ID NO 4
<211> LENGTH: 10
<212> TYPE: PRT
<213> ORGANISM: Humicola insolens

<400> SEQUENCE: 4

Pro Lys Ser Ile Trp Val Leu Ala Tyr Gln
1               5                   10

<210> SEQ ID NO 5
<211> LENGTH: 22
<212> TYPE: DNA
<213> ORGANISM: Humicola insolens
<220> FEATURE:
<221> NAME/KEY: misc_feature
<222> LOCATION: (11)..(11)
<223> OTHER INFORMATION: N = A, C, G, OR T
<220> FEATURE:
<221> NAME/KEY: misc_feature
<222> LOCATION: (14)..(14)
<223> OTHER INFORMATION: N = A, C, G, OR T
<220> FEATURE:
<221> NAME/KEY: misc_feature
<222> LOCATION: (17)..(17)
<223> OTHER INFORMATION: R = A or G
<220> FEATURE:
<221> NAME/KEY: misc_feature
<222> LOCATION: (20)..(20)
<223> OTHER INFORMATION: N = A, C, G, OR T

<400> SEQUENCE: 5
agttggcgcg nccngcraan gg                                          22

<210> SEQ ID NO 6
<211> LENGTH: 27
<212> TYPE: DNA
<213> ORGANISM: Humicola insolens

<400> SEQUENCE: 6
agctgtcgct gatggagccc gagaaga                                     27

<210> SEQ ID NO 7
<211> LENGTH: 27
<212> TYPE: DNA
<213> ORGANISM: Humicola insolens

<400> SEQUENCE: 7
gaaggcagtc cggccccatt gatatgc                                     27

<210> SEQ ID NO 8
<211> LENGTH: 27
<212> TYPE: DNA
<213> ORGANISM: Humicola insolens
```

-continued

```
<400> SEQUENCE: 8
gctccaaccc caagcagtac ctcatgc                                      27

<210> SEQ ID NO 9
<211> LENGTH: 27
<212> TYPE: DNA
<213> ORGANISM: Humicola insolens

<400> SEQUENCE: 9
ccgctacttc cgctcctacg tctccaa                                      27

<210> SEQ ID NO 10
<211> LENGTH: 36
<212> TYPE: DNA
<213> ORGANISM: Humicola insolens

<400> SEQUENCE: 10
acacaactgg ccatgaggtc ggttgctgct ttcctc                            36

<210> SEQ ID NO 11
<211> LENGTH: 36
<212> TYPE: DNA
<213> ORGANISM: Humicola insolens

<400> SEQUENCE: 11
cagtcacctc tagttattac ttacaaggat tcgagt                            36

<210> SEQ ID NO 12
<211> LENGTH: 25
<212> TYPE: DNA
<213> ORGANISM: Humicola insolens

<400> SEQUENCE: 12
actcaattta cctctatcca cactt                                        25

<210> SEQ ID NO 13
<211> LENGTH: 25
<212> TYPE: DNA
<213> ORGANISM: Humicola insolens

<400> SEQUENCE: 13
ctatagcgaa atggattgat tgtct                                        25
```

POLYPEPTIDES HAVING ARABINOFURANOSIDASE ACTIVITY AND POLYNUCLEOTIDES ENCODING SAME

CROSS-REFERENCE TO RELATED APPLICATIONS

This application is a divisional application of U.S. patent application Ser. No. 12/274,774, filed Nov. 20, 2008, now U.S. Pat. No. 8,034,599 which claims the benefit of U.S. Provisional Application No. 60/991,484, filed Nov. 30, 2007, which applications are incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to isolated polypeptides having alpha-L-arabinofuranosidase activity and isolated polynucleotides encoding the polypeptides. The invention also relates to nucleic acid constructs, vectors, and host cells comprising the polynucleotides as well as methods of producing and using the polypeptides.

2. Description of the Related Art

Plant cell wall polysaccharides generally constitute 90% of the plant cell wall and can be divided into three groups: cellulose, hemicellulose, and pectin. Cellulose represents the major constituent of cell wall polysaccharides. Hemicelluloses are the second most abundant constituent of plant cell walls. The major hemicellulose polymer is xylan. The structure of xylans found in cell walls of plants can differ significantly depending on their origin, but they always contain a beta-1,4-linked D-xylose backbone. The beta-1,4-linked D-xylose backbone can be substituted by various side groups, such as L-aribinose, D-galactose, acetyl, feruloyl, p-coumaroyl, and glucuronic acid residues.

Biodegradation of the xylan backbone depends on two classes of enzymes: endoxylanases and beta-xylosidases. Endoxylanases (EC 3.2.1.8) cleave the xylan backbone into smaller oligosaccharides, which can be further degraded to xylose by beta-xylosidases (EC 3.2.1.37). Other enzymes involved in the degradation of xylan include, for example, acetylxylan esterase, arabinase, alpha-L-arabinofuranosidase, alpha-glucuronidase, feruloyl esterase, and p-coumaric acid esterase.

Kaji and Tagawa, 1970, *Biochim. Biophys. Acta* 207 456-464, describe the purification, crystallization and amino acid composition of an alpha-L-arabinofuranosidase from *Aspergillus niger*. Kaji. and Yoshihara, 1971, *Biochim. Biophys. Acta* 250 367-371, describe the properties of an alpha-L-arabinofuranosidase from *Corticium rolfsii*. Tagawa and Kaji, 1969, *Carbohydr. Res.* 11: 293-301, describe the preparation of L-arabinose-containing polysaccharides and the action of an alpha-L-arabinofuranosidase on the polysaccharides. Filho et al., 1996, *Appl. Environ. Microbiol.* 62: 168-173, disclose the purification and characterization of two alpha-L-arabinofuranosidases from *Penicillium capsulatum*. WO 96/06935 discloses an arabinoxylan degrading enzyme from *Aspergillus niger*. WO 2006/125438 describes a *Penicillium capsulatum* alpha-L-arabinofuranosidase and polynucleotide thereof.

The present invention relates to polypeptides having alpha-L-arabinofuranosidase activity and polynucleotides encoding the polypeptides.

SUMMARY OF THE INVENTION

The present invention relates to isolated polypeptides having alpha-L-arabinofuranosidase activity selected from the group consisting of:

(a) a polypeptide comprising an amino acid sequence having at least 70% sequence identity to the mature polypeptide of SEQ ID NO: 2;

(b) a polypeptide encoded by a polynucleotide that hybridizes under at least medium-high stringency conditions with the mature polypeptide coding sequence of SEQ ID NO: 1 or its full-length complementary strand;

(c) a polypeptide encoded by a polynucleotide comprising a nucleotide sequence having at least 70% sequence identity to the mature polypeptide coding sequence of SEQ ID NO: 1; and (d) a variant comprising a substitution, deletion, and/or insertion of one or more (several) amino acids of the mature polypeptide of SEQ ID NO: 2.

The present invention also relates to isolated polynucleotides encoding polypeptides having alpha-L-arabinofuranosidase activity, selected from the group consisting of:

(a) a polynucleotide encoding a polypeptide comprising an amino acid sequence having at least 70% sequence identity to the mature polypeptide of SEQ ID NO: 2;

(b) a polynucleotide that hybridizes under at least medium-high stringency conditions with the mature polypeptide coding sequence of SEQ ID NO: 1 or its full-length complementary strand;

(c) a polynucleotide comprising a nucleotide sequence having at least 70% sequence identity to the mature polypeptide coding sequence of SEQ ID NO: 1; and (d) a polynucleotide encoding a variant comprising a substitution, deletion, and/or insertion of one or more (several) amino acids of the mature polypeptide of SEQ ID NO: 2.

The present invention also relates to nucleic acid constructs, recombinant expression vectors, recombinant host cells comprising the polynucleotides, and methods of producing a polypeptide having alpha-L-arabinofuranosidase activity.

The present invention also relates to methods of inhibiting the expression of a polypeptide in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is a siRNA or a miRNA molecule.

The present invention also relates to methods for degrading a material comprising a xylan.

The present invention also relates to plants comprising an isolated polynucleotide encoding such a polypeptide having alpha-L-arabinofuranosidase activity.

The present invention also relates to methods of producing such a polypeptide having alpha-L-arabinofuranosidase, comprising: (a) cultivating a transgenic plant or a plant cell comprising a polynucleotide encoding such a polypeptide having alpha-L-arabinofuranosidase activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 17 of SEQ ID NO: 2, wherein the gene is foreign to the nucleotide sequence.

BRIEF DESCRIPTION OF THE FIGURES

FIGS. 1A and 1B show the genomic DNA sequence and the deduced amino acid sequence of a Family 62 *Humicola insolens* DSM 1800 alpha-L-arabinofuranosidase (SEQ ID NOs: 1 and 2, respectively).

DEFINITIONS

Figure 2:
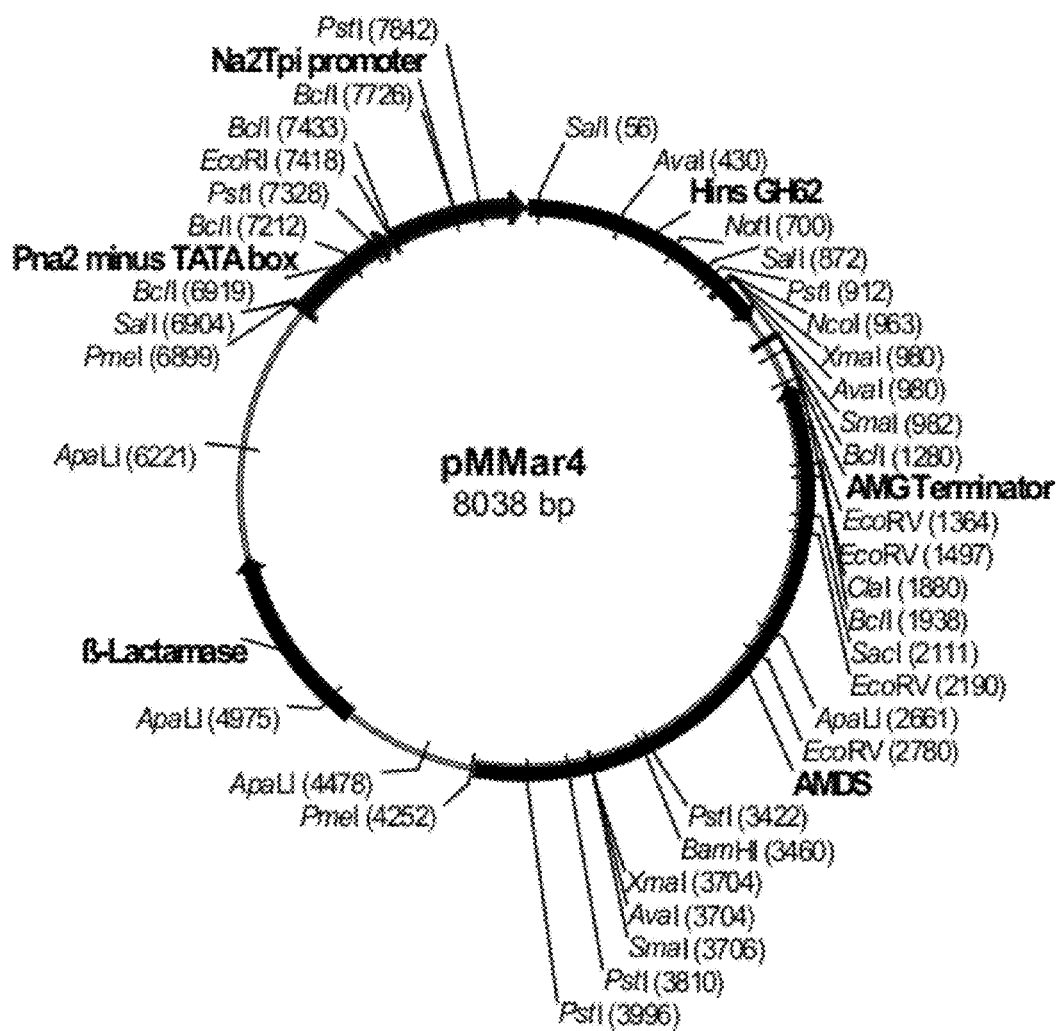
FIG. 2 shows a restriction map of pMMar4.

Alpha-L-arabinofuranosidase activity: The term "alpha-L-arabinofuranosidase activity" is defined herein as an alpha-L-arabinofuranoside arabinofuranohydrolase activity (EC 3.2.1.55) that catalyzes the hydrolysis of terminal non-reducing alpha-L-arabinofuranoside residues in alpha-L-arabinosides. The enzyme activity acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined according to the procedures described below or the procedure described in Example 10. The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the alpha-L-arabinofuranosidase activity of the mature polypeptide of SEQ ID NO: 2.

Preparation of Specific Arabinoxylan Oligosaccharides. Oligosaccharides Containing arabinosyl groups linked terminally (1→3) are prepared by incubating 1 g of water insoluble wheat arabinoxylan (Megazyme, Bray, County Wicklow, Ireland) in 100 ml of 0.1 M acetate pH 6.0 buffer with 6.67 g of SHEARZYME™ (*Aspergillus aculeatus* GH10 endo-1,4-beta-xylanase, Novozymes A/S, Bagsværd, Denmark) per kg of water insoluble wheat arabinoxylan for 2 hours at 30° C. Oligosaccharides containing arabinosyl groups linked internally (1→3) are prepared by incubating 1 g of water insoluble wheat arabinoxylan in 100 ml of 0.1 M sodium acetate pH 6.0 with 0.03 g of PENTOPAN™ MONO (*Thermomyces lanuginosus* GH11 endo-1,4-β-xylanase; Novozymes A/S, Bagsværd, Denmark) per kg of water insoluble wheat arabinoxylan for 2 hours at 30° C. Oligosaccharides containing arabinosyl groups linked internally (1→2) are prepared by incubating 1 g of water insoluble wheat arabinoxylan in 100 ml of 0.1 M sodium acetate pH 6.0 with 0.03 g of PENTOPAN™ MONO per kg of water insoluble wheat arabinoxylan and alpha-L-arabinofuranosidase per kg of water soluble wheat arabinoxylan for 2 hours at 30° C. To stop the enzymatic reaction, the mixture is heated at 100° C. for 10 minutes. The arabinoxylo-oligosaccharides are concentrated on a rotary evaporator and evaluated by $^1$H-NMR.

Determination of optimal reaction conditions. The optimal reaction conditions for an alpha-L-arabinofuranosidase is evaluated in a two-factor Box-Behnken response surface design templates (Montgomery, 2001, Design and analysis of experiments. Wiley, New York). Each template comprises several different combinations of pH (3-7) and reaction temperature (30-70° C.) with 3 center points. Water soluble wheat arabinoxylan (0.002 g; Megazyme, Bray, County Wicklow, Ireland) is dissolved in 2 ml of deionized water. The solution is then incubated with 0.1 g of enzyme protein per kg of water soluble wheat arabinoxylan per assay. Samples are withdrawn after exactly 24 hours of reaction and heated immediately at 100° C. for 10 minutes to stop the enzyme reaction. The samples are then centrifuged at 20,000×g for 10 minutes and the level of arabinose is determined in the supernatants by HPAEC analysis. The values reported are in mg per g of wheat arabinoxylan.

Mode of action of alpha-L-arabinofuranosidases. Alpha-L-arabinofuranosidase is added to 0.01 g of water soluble wheat arabinoxylan, 0.01 g of oligosaccharides containing either arabinosyl groups linked terminally (1→3), 0.01 g of oligosaccharides containing arabinosyl groups linked internally (1→3), or 0.01 g of oligosaccharides containing arabinosyl groups linked internally (1→2) in 1 ml of 0.1 M sodium acetate pH 6.0 for 2 hours at 40° C. The enzymatic reactions are inactivated at 100° C. for 10 minutes. Samples are concentrated on a rotary evaporator and analysed by $^1$H-NMR.

HPAEC. Hydrolysates (10 μl) are applied onto a BioLC system (Dionex Corporation, Sunnyvale, Calif., USA) fitted with a CARBOPAC™ PA1 guard column (4×250 mm) (Dionex Corporation, Sunnyvale, Calif., USA) combined with a CARBOPAC™ PA1 precolumn (4×50 mm). Arabinose is separated isocratically with 10 mM KOH for 15 minutes at a flow-rate of 1 ml per minute. Arabinose is detected by a pulsed electrochemical detector in the pulsed amperiometric detection mode. The potential of the electrode is programmed for +0.1 V (t=0-0.4 s) to −2.0 V (t=0.41-0.42 s) to 0.6 V (t=0.43 s) and finally −0.1 V (t=0.44-0.50 s), while integrating the resulting signal from t=0.2-0.4 s. Arabinose (Merck, Darmstadt, Germany) is used as a standard.

$^1$H-NMR analysis. All degradation products are lyophilized twice from 99.9% $D_2O$ and re-dissolved in 99.9% $D_2O$. Some hydrolysates are dialyzed (Spectra/Por membrane molecular weight cut-off 1000) to remove free arabinose prior to the spectral analysis. The $^1$H-NMR spectra are recorded at 30° C. in a Varian Mercury-VX instrument operated at 400 MHz and equipped with a 4-nucleus auto-switchable probe. Data are collected over 128-512 scans and the HDO signal is used as a reference signal (4.67 ppm).

Xylan-containing material: The term "xylan-containing material" is defined herein as any material comprising xylan as a constituent. Xylan is a plant cell wall polysaccharide containing a backbone of beta-1,4-linked xylose residues. Side chains of 4-O-methylglucuronic acid and arabinose are generally present in varying amounts, together with acetyl and feruloyl groups. Xylan is a major constituent of hemicellulose.

Family 62 or Family GH62: The term "Family 62" or "Family GH62" or "GH62" is defined herein as a polypeptide falling into the glycoside hydrolase Family 62 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having alpha-L-arabinofuranosidase activity that is in its final form following translation and any post-translational modifications, such as N-terminal processing, C-terminal truncation, glycosylation, phosphorylation, etc. In a preferred aspect, the mature polypeptide is amino acids 18 to 387 of SEQ ID NO: 2 based on the SignalP program that predicts amino acids 1 to 17 of SEQ ID NO: 2 are a signal peptide.

Mature polypeptide coding sequence: The term "mature polypeptide coding sequence" is defined herein as a nucleotide sequence that encodes a mature polypeptide having alpha-L-arabinofuranosidase activity. In a preferred aspect, the mature polypeptide coding sequence is nucleotides 52 to 1161 of SEQ ID NO: 1 based on the SignalP program that predicts nucleotides 1 to 51 of SEQ ID NO: 1 encode a signal peptide.

Identity: The relatedness between two amino acid sequences or between two nucleotide sequences is described by the parameter "identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Humicola insolens* alpha-L-arabinofuranosidase of SEQ ID NO: 2 or the mature polypeptide thereof.

Polypeptide fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has alpha-L-arabinofuranosidase activity. In a preferred aspect, a fragment contains at least 310 amino acid residues, more preferably at least 330 amino acid residues, and most preferably at least 350 amino acid residues of the mature polypeptide of SEQ ID NO: 2 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having alpha-L-arabinofuranosidase activity. In a preferred aspect, a subsequence contains at least 930 nucleotides, more preferably at least 990 nucleotides, and most preferably at least 1050 nucleotides of the mature polypeptide coding sequence of SEQ ID NO: 1 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having alpha-L-arabinofuranosidase activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptides Having Alpha-L-Arabinofuranosidase Activity

In a first aspect, the present invention relates to isolated polypeptides comprising an amino acid sequence having a degree of sequence identity to the mature polypeptide of SEQ ID NO: 2 of preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have alpha-L-arabinofuranosidase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof having alpha-L-arabinofuranosidase activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 18 to 387 of SEQ ID NO: 2, or an allelic variant thereof; or a fragment thereof having alpha-L-arabinofuranosidase activity. In another preferred aspect, the polypeptide comprises amino acids 18 to 387 of SEQ ID NO: 2. In another preferred aspect, the polypeptide consists of the amino acid sequence of SEQ ID NO: 2 or an allelic variant thereof; or a fragment thereof having alpha-L-arabinofuranosidase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 18 to 387 of SEQ ID NO: 2 or an allelic variant thereof; or a fragment thereof having alpha-L-arabinofuranosidase activity. In another preferred aspect, the polypeptide consists of amino acids 18 to 387 of SEQ ID NO: 2.

In a second aspect, the present invention relates to isolated polypeptides having alpha-L-arabinofuranosidase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) a subsequence of (i), or (iii) a full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.). A subsequence of the mature polypeptide coding sequence of SEQ ID NO: 1 contains at least 100 contiguous nucleotides or preferably at least 200 contiguous nucleotides. Moreover, the subsequence may encode a polypeptide fragment having alpha-L-arabinofuranosidase activity. In a preferred aspect, the complementary strand is the full-length complementary strand of the mature polypeptide coding sequence of SEQ ID NO: 1.

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides having alpha-L-arabinofuranosidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having alpha-L-arabinofuranosidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 52 to 1161 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pHinsGH62A which is contained in *E. coli* NRRL B-50075, wherein the polynucleotide sequence thereof encodes a polypeptide having alpha-L-arabinofuranosidase activity. In another preferred aspect, the nucleic acid probe is the mature polypeptide coding region contained in plasmid pHinsGH62A which is contained in *E. coli* NRRL B-50075.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having alpha-L-arabinofuranosidase activity encoded by polynucleotides comprising or consisting of nucleotide sequences that have a degree of sequence identity to the mature polypeptide coding sequence of SEQ ID NO: 1 of preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide. See polynucleotide section herein.

In a fourth aspect, the present invention relates to artificial variants comprising a substitution, deletion, and/or insertion of one or more (or several) amino acids of the mature polypeptide of SEQ ID NO: 2; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., alpha-L-arabinofuranosidase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 18 to 387 of SEQ ID NO: 2, is 10, preferably 9, more preferably 8, more preferably 7, more preferably at most 6, more preferably 5, more preferably 4, even more preferably 3, most preferably 2, and even most preferably 1.

Sources of Polypeptides Having Alpha-L-Arabinofuranosidase Activity

A polypeptide having alpha-L-arabinofuranosidase activity of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having alpha-L-arabinofuranosidase activity of the present invention may be a bacterial polypeptide. For example, the polypeptide may be a gram positive bacterial polypeptide such as a Bacillus, Streptococcus, Streptomyces, Staphylococcus, Enterococcus, Lactobacillus, Lactococcus, Clostridium, Geobacillus, or Oceanobacillus polypeptide having alpha-L-arabinofuranosidase activity, or a Gram negative bacterial polypeptide such as an E. coli, Pseudomonas, Salmonella, Campylobacter, Helicobacter, Flavobacterium, Fusobacterium, Ilyobacter, Neisseria, or Ureaplasma polypeptide having alpha-L-arabinofuranosidase activity.

In a preferred aspect, the polypeptide is a Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, or Bacillus thuringiensis polypeptide having alpha-L-arabinofuranosidase activity.

In another preferred aspect, the polypeptide is a Streptococcus equisimilis, Streptococcus pyogenes, Streptococcus uberis, or Streptococcus equi subsp. Zooepidemicus polypeptide having alpha-L-arabinofuranosidase activity.

In another preferred aspect, the polypeptide is a *Streptomyces achromogenes, Streptomyces avermitilis, Streptomyces coelicolor, Streptomyces griseus,* or *Streptomyces lividans* polypeptide having alpha-L-arabinofuranosidase activity.

A polypeptide having alpha-L-arabinofuranosidase activity of the present invention may also be a fungal polypeptide, and more preferably a yeast polypeptide such as a *Candida, Kluyveromyces, Pichia, Saccharomyces, Schizosaccharomyces,* or *Yarrowia* polypeptide having alpha-L-arabinofuranosidase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having alpha-L-arabinofuranosidase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having alpha-L-arabinofuranosidase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having alpha-L-arabinofuranosidase activity.

In another preferred aspect, the polypeptide is a *Humicola grisea, Humicola insolens,* or *Humicola lanuginosa* polypeptide.

In a more preferred aspect, the polypeptide is a *Humicola insolens* polypeptide having alpha-L-arabinofuranosidase activity. In a most preferred aspect, the polypeptide is a *Humicola insolens* DSM 1800 polypeptide having alpha-L-arabinofuranosidase activity, e.g., the polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having alpha-L-arabinofuranosidase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having alpha-L-arabinofuranosidase activity of the present invention.

In a preferred aspect, the nucleotide sequence comprises or consists of SEQ ID NO: 1. In another more preferred aspect, the nucleotide sequence comprises or consists of the sequence contained in plasmid pHinsGH62A which is contained in *E. coli* NRRL B-50075. In another preferred aspect, the nucleotide sequence comprises or consists of the mature polypeptide coding sequence of SEQ ID NO: 1. In another preferred aspect, the nucleotide sequence comprises or consists of nucleotides 52 to 1161 of SEQ ID NO: 1. In another more preferred aspect, the nucleotide sequence comprises or consists of the mature polypeptide coding sequence contained in plasmid pHinsGH62A which is contained in *E. coli* NRRL B-50075. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have alpha-L-arabinofuranosidase activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Humicola*, or another or related organism and thus, for example, may be an allelic or species variant of the polypeptide encoding region of the nucleotide sequence.

The present invention also relates to isolated polynucleotides comprising or consisting of nucleotide sequences that have a degree of sequence identity to the mature polypeptide coding sequence of SEQ ID NO: 1 of preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for alpha-L-arabinofuranosidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with the mature polypeptide coding sequence of SEQ ID NO: 1 or its full-length complementary strand; or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with the mature polypeptide coding sequence of SEQ ID NO: 1 or its full-length complementary strand; and (b) isolating the hybridizing polynucleotide, which encodes a polypeptide having alpha-L-arabinofuranosidase activity.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dana (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 17 of SEQ ID NO: 2. In another preferred aspect, the signal peptide coding sequence comprises or consists of nucleotides 1 to 51 of SEQ ID NO: 1.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus,* and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria,* and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis,* and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus,* and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45:

409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a Candida, Hansenula, Kluyveromyces, Pichia, Saccharomyces, Schizosaccharomyces, or Yarrowia cell.

In a most preferred aspect, the yeast host cell is a Saccharomyces carlsbergensis, Saccharomyces cerevisiae, Saccharomyces diastaticus, Saccharomyces douglasii, Saccharomyces kluyveri, Saccharomyces norbensis, or Saccharomyces oviformis cell. In another most preferred aspect, the yeast host cell is a Kluyveromyces lactis cell. In another most preferred aspect, the yeast host cell is a Yarrowia lipolytica cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

In an even more preferred aspect, the filamentous fungal host cell is an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

In a most preferred aspect, the filamentous fungal host cell is an Aspergillus awamori, Aspergillus fumigatus, Aspergillus foetidus, Aspergillus japonicus, Aspergillus nidulans, Aspergillus niger or Aspergillus oryzae cell. In another most preferred aspect, the filamentous fungal host cell is a Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, or Fusarium venenatum cell. In another most preferred aspect, the filamentous fungal host cell is a Bjerkandera adusta, Ceriporiopsis aneirina, Ceriporiopsis aneirina, Ceriporiopsis caregiea, Ceriporiopsis gilvescens, Ceriporiopsis panno-cinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238 023 and Yelton et al., 1984, Proceedings of the National Academy of Sciences USA 81: 1470-1474. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus Humicola. In a more preferred aspect, the cell is Humicola insolens. In a most preferred aspect, the cell is Humicola insolens DSM 1800.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having alpha-L-arabinofuranosidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having alpha-L-arabinofuranosidase activity of the present invention under conditions conducive for production of the polypeptide; and (b) recovering the polypeptide.

Removal or Reduction of Alpha-L-Arabinofuranosidase Activity

The present invention also relates to methods of producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of alpha-L-arabinofuranosidase activity by fermentation of a cell that produces both a polypeptide of the present invention as well as the protein product of interest by adding an effective amount of an agent capable of inhibiting alpha-L-arabinofuranosidase activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of alpha-L-arabinofuranosidase activity by cultivating the cell under conditions permitting the expression of the product, subjecting the resultant culture broth to a combined pH and temperature treatment so as to reduce the alpha-L-arabinofuranosidase activity substantially, and recovering the product from the culture broth. Alternatively, the combined pH and temperature treatment may be performed on an enzyme preparation recovered from the culture broth. The combined pH and temperature treatment may optionally be used in combination with a treatment with an alpha-L-arabinofuranosidase inhibitor.

In accordance with this aspect of the invention, it is possible to remove at least 60%, preferably at least 75%, more preferably at least 85%, still more preferably at least 95%, and most preferably at least 99% of the alpha-L-arabinofuranosidase activity. Complete removal of alpha-L-arabinofuranosidase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially alpha-L-arabinofuranosidase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The alpha-L-arabinofuranosidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from alpha-L-arabinofuranosidase activity that is produced by a method of the present invention.

Methods of Inhibiting Expression of a Polypeptide

The present invention also relates to methods of inhibiting the expression of a polypeptide in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing therapeutics. In one aspect, the invention provides methods to selectively degrade RNA using the dsRNAis of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. No. 6,506,559; U.S. Pat. No. 6,511,824; U.S. Pat. No. 6,515,109; and U.S. Pat. No. 6,489,127.

Compositions

The present invention also relates to compositions comprising a polypeptide of the present invention. Preferably, the compositions are enriched in such a polypeptide. The term "enriched" indicates that the alpha-L-arabinofuranosidase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium cul-*

*morum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola,* preferably *Humicola insolens* or *Humicola lanuginosa;* or *Trichoderma,* preferably *Trichoderma harzianum, Trichoderma koningii, Trichoderma longibrachiatum, Trichoderma reesei,* or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having alpha-L-arabinofuranosidase activity, or compositions thereof.

A polypeptide having alpha-L-arabinofuranosidase activity of the present invention may be used in several applications to degrade or convert a xylan-containing material by treating the material with an effective amount of the polypeptide (see, for example, WO 2002/18561). The polypeptides of the present invention are preferably used in conjunction with other xylan degrading enzymes such as xylanases, acetylxylan esterases, arabinofuranosidases, xylosidases, feruloyl esterases, glucuronidases, and a combination thereof, in processes wherein xylan has to be degraded. As a consequence of the deacylating reaction the xylan becomes better accessible for xylanases and other xylan-degrading enzymes.

The polypeptides having alpha-L-arabinofuranosidase activity are useful in a number of applications: in vivo modification of xylan containing animal feeds to improve digestability; general applications resulting from biomass degradation or conversion to fermentable sugars in the production of, for example, fuel and/or potable ethanol; processing aids used in pulp and paper de-lignification; component of enzymatic scouring systems for textiles; food applications, e.g., baking, in combination with other enzymatic functionalities to improve the physical properties of baked goods; and laundry detergent applications in combination with other enzyme functionalities.

The polypeptides may be used in methods for the treatment of Kraft pulp according to U.S. Pat. No. 5,658,765. Generally Kraft pulp is generally treated with xylanase in order to remove lignin in the preparation of paper products. The effectiveness of xylanase is greatly increased when pulp is treated with alpha-L-arabinofuranosidase either before or at the same time as the xylanase treatment.

The polypeptides may also be used in processes for producing xylose or xylo-oligosaccharide according to U.S. Pat. No. 5,658,765.

The polypeptides may also be used as feed enhancing enzymes that improve feed digestibility to increase the efficiency of its utilization according to U.S. Pat. No. 6,245,546. The use of alpha-L-arabinofuranosidase in feed can decrease the solubility of the feed components thereby diminishing the viscosity and reducing anti-nutritional effect of pentosanes.

The polypeptides may also be used in baking according to U.S. Pat. No. 5,693,518.

The polypeptides may further be used in brewing according to WO 2002/24926, where combinations of this enzyme with other enzymes can be used to degrade biological cell-wall material to increase digestibility or flow characteristics in applications relating to the preparation of fruit juices or beer.

Consequently, the present invention also relates to methods for degrading a xylan, comprising treating a xylan-containing material with such a polypeptide having alpha-L-arabinofuranosidase activity. In a preferred aspect, the xylan-containing material is further treated with one or more xylan degrading enzymes.

Signal Peptide

The present invention also relates to nucleic acid constructs comprising a gene encoding a protein, wherein the gene is operably linked to a nucleotide sequence encoding a signal peptide comprising or consisting of amino acids 1 to 17 of SEQ ID NO: 2, wherein the gene is foreign to the nucleotide sequence.

In a preferred aspect, the nucleotide sequence comprises or consists of nucleotides 1 to 51 of SEQ ID NO: 1.

The present invention also relates to recombinant expression vectors and recombinant host cells comprising such nucleic acid constructs.

The present invention also relates to methods of producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Humicola insolens* DSM 1800 was used as the source of a Family 62 gene encoding a polypeptide having alpha-L-arabinofuranosidase activity. *Aspergillus niger* MBin120 strain (WO 2004/090155) was used for expression of the *Humicola insolens* gene encoding the polypeptide having alpha-L-arabinofuranosidase activity.

Media

PDA plates were composed per liter of 39 g of potato dextrose agar.

YP medium was composed per liter of 10 g of yeast extract and 20 g of Bacto peptone.

COVE A urea– acetamide+ plates were composed per liter of 20 ml of COVE A salts solution, 220 g of sorbitol, 10 g of glucose, 10 ml of 1 M acetamide, and 30 g of Bacto agar; pH 5.2.

COVE A salts solution was composed per liter of 26 g of KCl, 26 g of $MgSO_4$, 76 g of $KH_2PO_4$, and 50 ml of COVE A trace elements solution.

COVE A trace elements solution was composed per liter of 0.04 g of $Na_2B_4O_7.10H_2O$, 0.4 g of $CuSO_4.5H_2O$, 0.8 g of $FeSO_4.7H_2O$, 0.7 g of $MnSO_4.H_2O$, 0.8 g of $Na_2MoO_2.2H_2O$, 10 g of $ZnSO_4.7H_2O$, and 10 g of citric acid.

M410 medium was composed per liter of 50 g of maltose, 50 g of glucose, 2 g of $MgSO_4.7H_2O$, 2 g of $KH_2PsO_4$, 4 g of citric acid anhydrous powder, 8 g of yeast extract, 2 g of urea, 0.5 g of AMG trace metals solution, and 0.5 g of $CaCl_2$; pH 6.0.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, and 3 g of citric acid.

LB medium was composed per liter of 10 g of tryptone, 5 g of yeast extract, and 5 g of NaCl.

Example 1

Identification of a *Humicola insolens* GH62A Polypeptide Having Alpha-L-Arabinofuranosidase Activity Protein Fractionation of ULTRAFLO L®. A 2 ml aliquot of ULTRAFLO® L (Novozymes A/S, Bagsværd, Denmark) was first buffer-exchanged into 150 mM sodium chloride-20 mM sodium acetate pH 5 using a HIPREP™ 26/10 Desalting Column (GE Healthcare, Piscataway, N.J., USA). The resulting buffer-exchanged material (18.5 ml) was then concentrated to 3 ml by ultrafiltration with a VIVASPIN® 20 spin column equipped with a 3,000 Dalton molecular weight cut-off membrane (Vivascience AG, Hannover, Germany). A 2 ml aliquot of the buffer-exchanged and concentrated ULTRA-FLO® L material was then fractionated by size-exclusion chromatography over a HILOAD™ 26/60 SUPERDEX™ 200 prep grade size exclusion column (GE Healthcare, Piscataway, N.J., USA), under the same buffer conditions with isocratic elution. Fractions showing UV absorbance at 280 nm were combined into six separate pools from varying elution times, ranging from 20-40 ml total volume each. Pooled fractions were concentrated to between 1-5 ml by ultrafiltration with a VIVASPIN® 20 spin column equipped with a 3,000 Da molecular weight cut-off membrane. Twenty µl of each concentrated pooled fraction was separated on a CRITERION® 8-16% Tris-HCl SDS-PAGE gel (Bio-Rad Laboratories, Inc., Hercules, Calif., USA) according to the manufacturer's suggested conditions. PRECISION PLUS PROTEIN™ standards (Bio-Rad Laboratories, Inc., Hercules, Calif., USA) were used as molecular weight markers. The gel was removed from the cassette and was stained with Coomassie Blue (G250) protein stain (BIO-SAFE™ Coomassie Stain, Bio-Rad Laboratories, Inc., Hercules, Calif., USA), and visible bands were excised with a razor blade for protein identification analysis.

In-gel digestion of polypeptides for peptide sequencing. A MultiPROBE® II Liquid Handling Robot (PerkinElmer Life and Analytical Sciences, Boston, Mass., USA) was used to perform the in-gel digestions. A 45 kDa protein gel band was reduced with 50 µl of 10 mM dithiothreitol (DTT) in 100 mM ammonium bicarbonate pH 8.0 for 30 minutes. Following reduction, the gel piece was alkylated with 50 µl of 55 mM iodoacetamide in 100 mM ammonium bicarbonate pH 8.0 for 20 minutes. The dried gel piece was allowed to swell in 25 µl of a trypsin digestion solution (6 ng/µl sequencing grade trypsin; Promega, Madison, Wis., USA) in 50 mM ammonium bicarbonate pH 8 for 30 minutes at room temperature, followed by an 8 hour digestion at 40° C. Each of the reaction steps described above was followed by numerous washes and pre-washes with the appropriate solutions following the manufacturer's standard protocol. Fifty µl of acetonitrile was used to de-hydrate the gel piece between reactions and the gel piece was air dried between steps. Peptides were extracted twice with 1% formic acid/2% acetonitrile in HPLC grade water for 30 minutes. Peptide extraction solutions were transferred to a 96 well skirted PCR type plate (ABGene, Rochester, N.Y., USA) that had been cooled to 10-15° C. and covered with a 96-well plate lid (PerkinElmer Life and Analytical Sciences, Boston, Mass., USA) to prevent evaporation. Plates were further stored at 4° C. until mass spectrometry analysis could be performed.

Protein Identification. For de novo peptide sequencing by tandem mass spectrometry, a Q-TOFMICRO™, a hybrid orthogonal quadrupole time-of-flight mass spectrometer (Waters Micromass MS Technologies, Milford, Mass.) was used for LC/MS/MS analysis. The Q-TOF MICRO™ was fitted with an ULTIMATE™ capillary and nano-flow HPLC system, which was coupled with a FAMOS™ micro autosampler and a SWITCHOS™ II column switching device (LCPackings/Dionex, Sunnyvale, Calif., USA) for concentrating and desalting samples. Samples were loaded onto a guard column (300 µm ID×5 cm, PEPMAP™ C18) fitted in the injection loop and washed with 0.1% formic acid in water at 40 µl per minute for 2 minutes using a Switchos II pump. Peptides were separated on a 75 µm ID×15 cm, C18, 3 µm, 100 Å PEPMAP™ (LC Packings, San Francisco, Calif., USA) nanoflow fused capillary column at a flow rate of 175 nl/minute from a split flow of 175 µl/minute using a NAN-75 calibrator (Dionex, Sunnyvale, Calif., USA). A step elution gradient of 5% to 80% acetonitrile in 0.1% formic acid was applied over a 45 minute interval. The column eluent was monitored at 215 nm and introduced into the Q-TOF MICRO™ through an electrospray ion source fitted with the nanospray interface. The Q-TOF MICRO™ was fully microprocessor controlled using MASSLYNX™ software version 4.1 (Waters Micromass MS Technologies, Milford, Mass., USA). Data was acquired in survey scan mode and from a mass range of m/z 400 to 1990 with the switching criteria for MS to MS/MS to include an ion intensity of greater than 10.0 counts per second and charge states of +2, +3, and +4. Analysis spectra of up to 4 co-eluting species with a scan time of 1.9 seconds and inter-scan time of 0.1 seconds could be obtained. A cone voltage of 45 volts was typically used and the collision energy was programmed to be varied according to the mass and charge state of the eluting peptide and in the range of 10-60 volts. The acquired spectra were combined, smoothed, and centered in an automated fashion and a peak list generated. This peak list was searched against selected databases using PROTEINLYNX™ Global Server 2.2.05 software (Waters Micromass MS Technologies, Milford, Mass., USA) and PEAKS Studio version 4.5 SP1 (Bioinformatic Solutions Inc., Waterloo, Ontario, Canada) Results from the PROTEINLYNX™ and PEAKS Studio searches were evaluated and un-identified proteins were analyzed further by evaluating the MS/MS spectrums of each ion of interest and de novo sequence was determined by identifying the y and b ion series and matching mass differences to the appropriate amino acid.

Peptide sequences determined from de novo sequencing by mass spectrometry were obtained from several multiply charged ions for the in-gel digested 45 kDa polypeptide gel band. A doubly charged tryptic peptide ion of 604.26 m/z sequence was determined to be [[ILE/Leu] or Asp]-Thr-Ser-Glu-Asn-Asn-Pro-Phe-Ala-Gly-Arg (amino acids 249 to 259 of SEQ ID NO: 2). Another doubly charged tryptic peptide ion of 698.32 m/z sequence was determined to be [Gln/Lys]-Tyr-[Ile/Leu]-Met-[Ile/Leu]-Val-Glu-Ser-[Ile/Leu]-Gly-Ser-Arg (amino acids 218 to 229 of SEQ ID NO: 2). Another doubly charged tryptic peptide ion of 711.32 m/z sequence was determined to be Asn-[Ile/Leu]-Trp-Val-[Ile/Leu]-Ala-Tyr-[Gln/Lys]-Trp-Gly-Arg (amino acids 105 to 115 of SEQ ID NO: 2). Another doubly charged tryptic peptide ion of 726.84 m/z sequence was determined to be Ala-Ala-Val-Ala-Pro-Thr-Leu-Phe-Tyr-Phe-[Gln/Lys]-Pro-Lys (amino acids 92 to 104 of SEQ ID NO: 2). Another doubly charged tryptic peptide ion of 1005.42 m/z sequence was determined to be Asn-Asp-[Ile/Leu]-Phe-Glu-Ala-Val-[Gln/Lys]-Val-Tyr-Thr-Ile-Asp-Gly-Ser-Asn-Pro-[Gln/Lys] (amino acids 200 to 217 of SEQ ID NO: 2). [Ile/Leu] and [Gln/Lys] could not be distinguished because they had equivalent masses.

Example 2

Humicola insolens DSM 1800 Genomic DNA Extraction

Humicola insolens DSM 1800 was grown on PDA plates at 45° C. to confluence. Three 4 mm² squares were cut from the PDA plates and inoculated into 25 ml of YP medium containing 2% glucose in a baffled 125 ml shake flask at 41° C. and 200 rpm for 2 days with shaking at 200 rpm. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and total DNA was isolated using a DNEASY® Plant Maxi Kit (QIAGEN Inc., Valencia, Calif., USA).

Example 3

Isolation of a Partial Fragment of a GH62A Alpha-L-Arabinofuranosidase Gene from Humicola insolens DSM 1800

Using the Consensus-degenerate hybrid oligonucleotide primer program (CODEHOP; Rose et al., 1998, Nucleic Acids Research 26: 1628-1635), degenerate primers were designed to regions of homology with related GH62 sequences based on the identified peptide fragments described in Example 1. Degenerate primers employed to generate a fragment of the Humicola insolens GH62A alpha-L-arabinofuranosidase gene were:

```
Primer HinsGH62sense1:
                                    (SEQ ID NO: 3)
5'-CCAAGTCGATCTGGGTNCTCGCNTAYCA-3'

Protein translation for degenerate
primer HinsGH62sense1:
                                    (SEQ ID NO: 4)
PKSIWVLAYQ Primer HinsGH62anti1:
                                    (SEQ ID NO: 5)
5'-AGTTGGCGCGNCCNGCRAANGG-3'

Protein translation for degenerate
primer HinsGH62anti1:
PFAGRAN
```

To obtain the initial DNA fragment of the Humicola insolens GH62A alpha-L-arabinofuranosidase gene, gradient PCR was performed at 6 different annealing temperatures ranging form 40° C. to 60° C. Amplification reactions (25 µl) were composed of 80 ng of Humicola insolens DSM 1800 genomic DNA as template, 0.4 mM each of dATP, dTTP, dGTP, and dCTP, 50 pmol each of primer HinsGH62sense1 and primer HinsGH62anti1, 1× ADVANTAGE® GC-Melt LA Buffer (Clontech Laboratories, Inc., Mountain View, Calif., USA), and 1.25 units of ADVANTAGE® GC Genomic Polymerase Mix (Clontech Laboratories, Inc., Mountain View, Calif., USA). The amplification reactions were performed using an EPPENDORF® MASTERCYCLER® 5333 (Eppendorf Scientific, Inc., Westbury, N.Y., USA) programmed for pre-denaturing at 95° C. for 1 minute; 30 cycles each at a denaturing temperature of 95° C. for 30 seconds; annealing temperature of 50° C.+/−10° C. for 30 seconds (6 gradient options) and elongation at 72° C. for 1 minute; and final elongation at 72° C. for 6 minutes.

The reaction products were isolated by 1.0% agarose gel electrophoresis in TBE (10.8 g of Tris base, 5.5 g of boric acid and 4 ml of 0.5 M EDTA pH 8.0 per liter) buffer. A PCR product band of approximately 500 bp from an annealing temperature of 59.8° C. was excised from the gel, purified using a QIAQUICK® Gel Extraction Kit (QIAGEN Inc., Valencia, Calif., USA) according to the manufacturer's instructions, and sequenced with a Perkin-Elmer Applied Biosystems Model 377 XL Automated DNA Sequencer (Perkin-Elmer/Applied Biosystems, Inc., Foster City, Calif., USA) using dye-terminator chemistry (Giesecke et al., 1992, Journal of Virology Methods 38: 47-60) and primer walking strategy using primers HinsGH62sense1 and Primer HinsGH62anti1.

Example 4

Identification of a Full-Length Humicola insolens GH62A Alpha-L-Arabinofuranosidase Gene The full-length Family 62 alpha-L-arabinofuranosidase gene was identified from Humicola insolens DSM 1800 using a GENOMEWALKER™ Universal Kit (Clontech Laboratories, Inc., Mountain View, Calif., USA) according to the manufacturer's instructions. Briefly, total genomic DNA from Humicola insolens DSM 1800 was digested separately with four different restriction enzymes (Dra I, Eco RV, Pvu II, and Stu I) that leave blunt ends. Each batch of digested genomic DNA was then ligated separately to the GENOMEWALKER™ Adaptor (Clontech Laboratories, Inc., Mountain View, Calif., USA) to create four libraries. These four libraries were then employed as templates in PCR reactions using four gene-specific primers shown below, two for a primary and secondary PCR amplifying upstream of the fragment through the 5' end encoding the N-terminus of the alpha-L-arabinofuranosidase and two for primary and secondary PCR amplifying downstream of the fragment through the 3' end encoding the C-terminus of the alpha-L-arabinofuranosidase. The following primers were designed based on the partial Family 62 alpha-L-arabinofuranosidase gene sequence from *Humicola insolens* described in Example 3.

```
N-terminus:
Primer Hins_GH62_GSP1_R (primary):
                                    (SEQ ID NO: 6)
5'-AGCTGTCGCTGATGGAGCCCGAGAAGA-3'

Primer Hins_GH62_GSP2_R (secondary):
                                    (SEQ ID NO: 7)
5'-GAAGGCAGTCCGGCCCCATTGATATGC-3'

C-terminus:
Primer Hins_GH62_GSP1_F (primary):
                                    (SEQ ID NO: 8)
5'-GCTCCAACCCCAAGCAGTACCTCATGC-3'

Primer Hins_GH62_GSP2_F (secondary):
                                    (SEQ ID NO: 9)
5'-CCGCTACTTCCGCTCCTACGTCTCCAA-3'
```

The primary amplifications were composed of 1 µl (approximately 6 ng) of each library as template, 0.4 mM each of dATP, dTTP, dGTP, and dCTP, 10 pmol of Adaptor Primer 1 (Clontech Laboratories, Inc., Mountain View, Calif., USA), 50 pmol of primer Hins_GH62_GSP1_R or Hins_GH62_GSP1_F, 1× ADVANTAGE® GC-Melt LA Buffer (Clontech Laboratories, Inc., Mountain View, Calif., USA), and 1.25 units of ADVANTAGE® GC Genomic Polymerase Mix in a final volume of 25 µl. The amplifications were performed using an EPPENDORF® MASTERCYCLER® 5333 programmed for pre-denaturing at 95° C. for 1 minute; 7 cycles each at a denaturing temperature of 95° C. for 25 seconds; annealing and elongation at 72° C. for 5 minutes; and 32 cycles each at a denaturing temperature of 95° C. for 25 seconds; annealing and elongation at 67° C. for 5 minutes; and final elongation at 67° C. for 7 minutes.

The secondary amplifications were composed of 1 µl of each primary PCR product as template, 0.4 mM each of dATP, dTTP, dGTP, and dCTP, 10 pmol of Adaptor Primer 2 (Clontech Laboratories, Inc., Mountain View, Calif., USA), 50 pmol of primer Hins_GH62_GSP2_R or Hins_GH62_GSP2_F, 1× ADVANTAGE® GC-Melt LA Buffer, and 1.25 units of ADVANTAGE® GC Genomic Polymerase Mix in a final volume of 25 µl. The amplifications were performed using an EPPENDORF® MASTERCYCLER® 5333 programmed for pre-denaturing at 95° C. for 1 minute; 5 cycles each at a denaturing temperature of 95° C. for 25 seconds; annealing and elongation at 72° C. for 5 minutes; and 20 cycles each at a denaturing temperature of 95° C. for 25 seconds; annealing and elongation at 67° C. for 7 minutes; and final elongation at 67° C. for 5 minutes.

The reaction products were isolated by 1.0% agarose gel electrophoreisis in TBE buffer. From the 5' end PCR amplification, a 600 bp product band from the Dra I library was excised from the gel, purified using a QIAQUICK® Gel Extraction Kit according to the manufacturer's instructions, and sequenced. From the 3' end PCR amplification, a 1.8 kb product band from the Dra I library was excised from the gel and a 700 bp product band from the Eco RV library was excised from the gel, purified using a QIAQUICK® Gel Extraction Kit according to the manufacturer's instructions, and sequenced.

DNA sequencing of the PCR fragments was performed with a Perkin-Elmer Applied Biosystems Model 377 XL Automated DNA Sequencer using dye-terminator chemistry (Giesecke et al., 1992, supra) and primer walking strategy. Adaptor Primer 2, primer Hins_GH62_GSP2_R, and primer Hins_GH62_GSP2_F were used for sequencing.

Nucleotide sequence data were scrutinized for quality and all sequences were compared to each other with assistance of PHRED/PHRAP software (University of Washington, Seattle, Wash., USA). The PCR fragment sequence results were compared and aligned with the partial Family 62 alpha-L-arabinofuranosidase gene sequence from *Humicola insolens* described in Example 3. A gene model was constructed based on the gene fragments obtained here and in Example 3 allowing determination of the 5' and 3' ends of the gene with other homologous Family 62 alpha-L-arabinofuranosidases.

Example 5

Cloning of the Full-Length *Humicola insolens* GH62A Alpha-L-Arabinofuranosidase Gene and Construction of an *Aspergillus niger* Expression Vector Two synthetic oligonucleotide primers shown below were designed to PCR amplify the full-length *Humicola insolens* DSM 1800 alpha-L-arabinofuranosidase gene from the genomic DNA prepared in Example 2. An InFusion Cloning Kit (BD Biosciences, Palo Alto, Calif., USA) was used to clone the fragment directly into the expression vector pBM120a (WO 2006/078256).

```
BDinfGH62senseNCO:
                                    (SEQ ID NO: 10)
5'-ACACAACTGGCCATGAGGTCGGTTGCTGCTTTCCTC-3'

BDinfantiGH62PAC1:
                                    (SEQ ID NO: 11)
5'-CAGTCACCTCTAGTTATTACTTACAAGGATTCGAGT-3'
```

Bold letters represent coding sequence. The remaining sequence is homologous to the insertion sites of pBM120a.

Fifty picomoles of each of the primers above were used in a PCR reaction composed of 80 ng of *Humicola insolens* genomic DNA, 1× ADVANTAGE® GC-Melt LA Buffer, 0.4 mM each of dATP, dTTP, dGTP, and dCTP, and 1.25 units of ADVANTAGE® GC Genomic Polymerase Mix in a final volume of 25 µl. The amplification was performed using an EPPENDORF® MASTERCYCLER® 5333 programmed for 1 cycle at 94° C. for 1 minute; 5 cycles each at 94° C. for 30 seconds, 50° C. for 30 seconds, and 72° C. for 90 seconds; and 30 cycles each at 94° C. for 30 seconds, 60° C. for 30 seconds, and 72° C. for 90 seconds; and a final elongation at 72° C. for 5 minutes. The heat block then went to a 4° C. soak cycle.

The reaction products were isolated by 1.0% agarose gel electrophoresis in TBE buffer where an approximately 1.1-1.2 kb product band was excised from the gel, and purified using a QIAQUICK® Gel Extraction Kit according to the manufacturer's instructions.

Plasmid pBM120a was digested with Nco I and Pac I, isolated by 1.0% agarose gel electrophoresis in TBE buffer, and purified using a QIAQUICK® Gel Extraction Kit according to the manufacturer's instructions.

The gene fragment and the digested vector were ligated together using an InFusion Cloning Kit (BD Biosciences, Palo Alto, Calif., USA) resulting in pMMar4 (FIG. 2) in which transcription of the alpha-L-arabinofuranosidase gene was under the control of a hybrid of promoters from the genes for *Aspergillus niger* neutral alpha-amylase and *Aspergillus oryzae* triose phosphate isomerase (NA2-tpi promoter). The ligation reaction (20 µl) was composed of 1× InFusion Buffer (BD Biosciences, Palo Alto, Calif., USA), 1×BSA (BD Biosciences, Palo Alto, Calif., USA), 1 µl of InFusion enzyme (diluted 1:10) (BD Biosciences, Palo Alto, Calif., USA), 106 ng of pBM120a digested with Nco I and Pac I, and 163 ng of the purified *Humicola insolens* PCR product. The reaction was incubated at room temperature for 30 minutes. Two µl of the reaction was used to transform *E. coli* XL10 SOLOPACK® Gold Supercompetent cells (Stratagene, La Jolla, Calif., USA). An *E. coli* transformant containing pMMar4 was detected by restriction digestion and plasmid DNA was prepared using a BIOROBOT® 9600 (QIAGEN Inc., Valencia, Calif., USA). The *Humicola insolens* GH62A insert in pMMar4 was confirmed by DNA sequencing with a Perkin-Elmer Applied Biosystems Model 377 XL Automated DNA Sequencer using dye-terminator chemistry (Giesecke et al., 1992, supra) and primer walking strategy. Primers 996271 Na2tpi promoter fwd and 996270 AMG rev, shown below, were used for sequencing.

```
996271 Na2tpi promoter fwd:
                                (SEQ. ID NO: 12)
5'-ACTCAATTTACCTCTATCCACACTT-3'

996270 AMG rev:
                                (SEQ. ID NO: 13)
5'-CTATAGCGAAATGGATTGATTGTCT-3'
```

Figure 3:
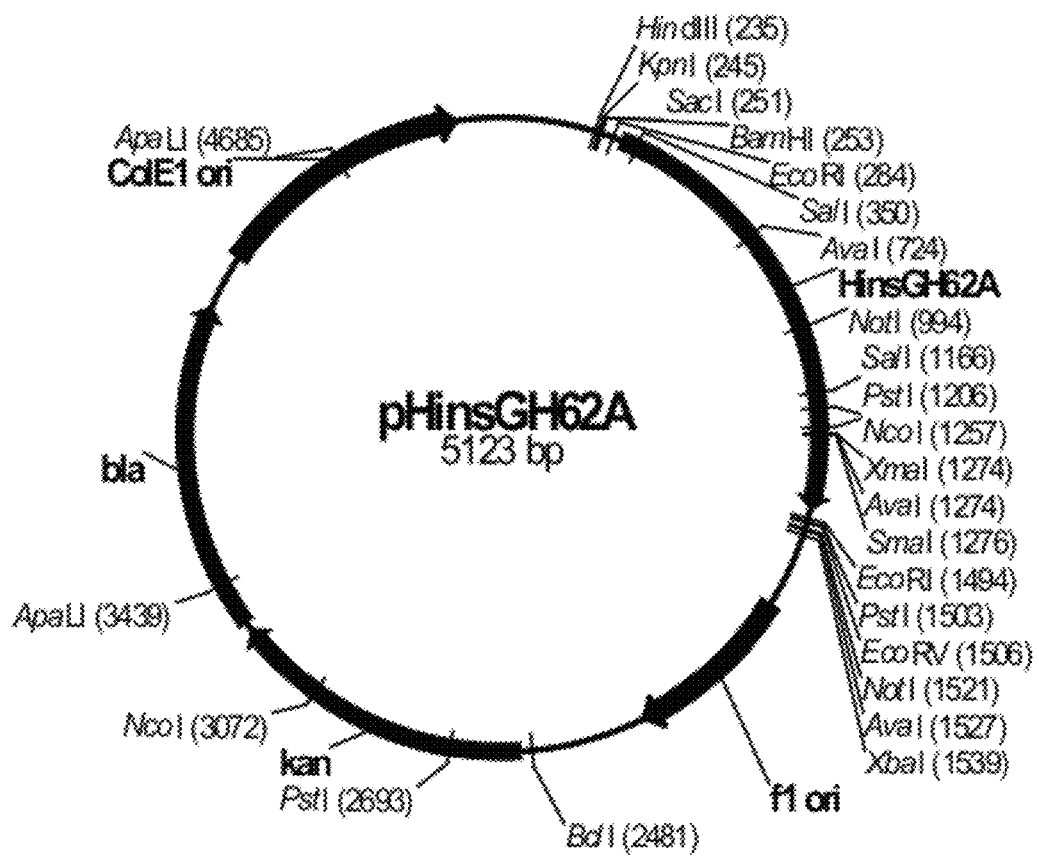
FIG. 3 shows a restriction map of pHinsGH62A.

A clone containing pMMar4 was picked into 2×50 ml of LB medium supplemented with 100 µg of ampicillin per ml and grown overnight in 250 ml glass beakers at 37° C. and 200 rpm agitation. Plasmid pMMar4 was isolated from broth using a QIAGEN® Midi Kit according to the manufacturer's instructions. Plasmid pMMar4 was digested with Pme I and isolated by 1.0% agarose gel electrophoresis in TBE buffer, and the fragment containing the GH62A alpha-L-arabinofuranosidase gene was purified using a QIAQUICK® Gel Extraction Kit according to the manufacturer's instructions in preparation for transforming *Aspergillus niger* MBin120 protoplasts. The fragment of approximately 1.1-1.2 kb was cloned into pCR®2.1-TOPO® vector (Invitrogen, Carlsbad, Calif., USA) using a TOPO® TA CLONING Kit, to generate pHinsGH62A (FIG. 3). The *Humicola insolens* GH62A insert in pHinsGH62A was confirmed by DNA sequencing. *E. coli* pHinsGH62A was deposited with the Agricultural Research Service Patent Culture Collection, Northern Regional Research Center, Peoria, Ill., on Nov. 20, 2007.

Example 6

Characterization of the Full-Length *Humicola insolens* Genomic Sequence Encoding a GH62A Polypeptide Having Alpha-L-Arabinofuranosidase Activity Nucleotide sequence data (Example 5) were scrutinized for quality and all sequences were compared to each other with assistance of PHRED/PHRAP software (University of Washington, Seattle, Wash., USA).

Figure 1A:
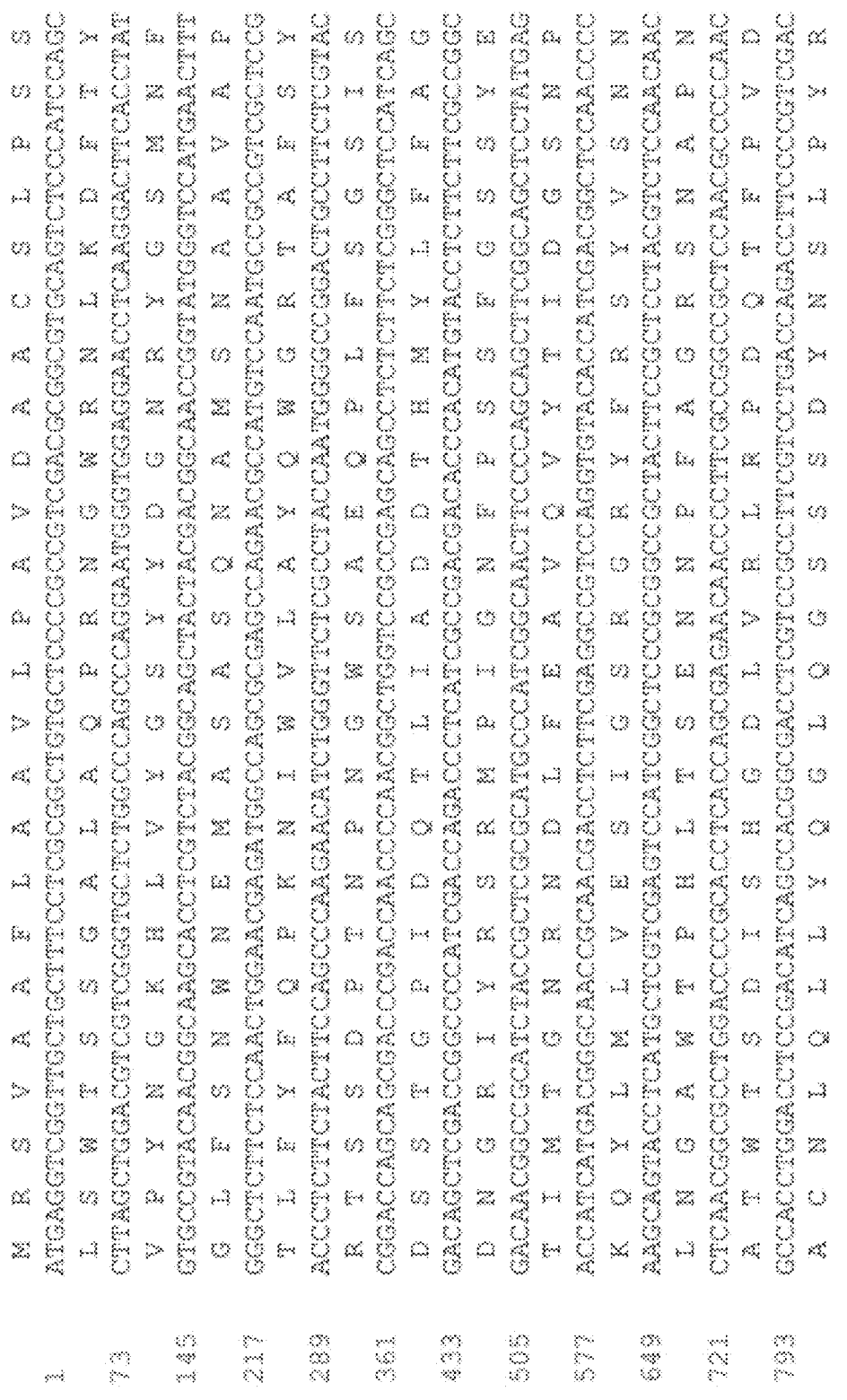

The nucleotide sequence (SEQ ID NO: 1) and deduced amino acid sequence (SEQ ID NO: 2) are shown in FIGS. 1A and 1B. The genomic fragment encodes a polypeptide of 387 amino acids. The % G+C content of the full-length coding sequence and the mature coding sequence are 64.9% and 65%, respectively. Using the SignalP software program (Nielsen et al., 1997, *Protein Engineering* 10:1-6), a signal peptide of 17 residues was predicted. The predicted mature protein contains 370 amino acids with a molecular mass of 40.3 kDa.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the mature polypeptide of the *Humicola insolens* Family 62 alpha-L-arabinofuranosidase gene shared 65.7% identity (excluding gaps) to the deduced amino acid sequence of an *Aspergillus niger* arabinoxylan degrading enzyme (GeneSeqP accession number AAR94170).

Example 7

Expression of the *Humicola insolens* GH62A Alpha-L-Arabinofuranosidase Gene in *Aspergillus niger* MBin120

*Aspergillus niger* MBin120 protoplasts were prepared according to the method of Christensen et al., 1988, *Bio/Technology* 6: 1419-1422. Four µg of Pme I digested pMMar4 were used to transform *Aspergillus niger* MBin120.

The transformation of *Aspergillus niger* MBin120 with the Pme I digested pMMar4 yielded about 50 transformants. Twenty-two transformants were isolated to individual COVE A urea– acetamide+ plates. Two 3 mm square agar plugs were cut from confluent COVE A urea– acetamide+ plates of the 22 transformants and inoculated separately into 25 ml of M410 medium in 125 ml plastic shake flasks and incubated at 34° C., 250 rpm. After 5 days incubation, 6 µl of supernatant from each culture were analyzed by SDS-PAGE using a CRITERION® 8-16% Tris-HCl SDS-PAGE gel with a CRITERION® Cell (Bio-Rad Laboratories, Inc., Hercules, Calif., USA), according to the manufacturer's instructions. The resulting gel was stained with BIO-SAFE™ Coomassie Stain (Bio-Rad Laboratories, Inc., Hercules, Calif., USA). SDS-PAGE profiles of the cultures showed approximately half of the transformants had a major band of approximately 45 kDa. One transformant designated *Aspergillus niger* MMar202 was chosen for expression of the *Humicola insolens* GH62A polypeptide having alpha-L-arabinofuranosidase activity in *Aspergillus niger*.

Example 8

Fermentation of *Aspergillus niger* MMar202

Shake flask medium was composed per liter of 70 g of sucrose and 100 g of soy concentrate. Trace metals solution was composed per liter of 13.8 g of $FeSO_4.7H_2O$, 14.3 g of $ZnSO_4.7H_2O$, 11.6 g of $MnSO_4.H_2O$, 2.5 g of $CuSO_4.5H_2O$, 0.5 g of $NiCl_2.6H_2O$ and 3.3 g of citric acid monohydrate.

One hundred ml of shake flask medium was added to a 500 ml shake flask. The shake flask was inoculated with 200 µl from a glycerol spore stock of *Aspergillus niger* MMar202 and incubated at 30° C. on an orbital shaker at 220 rpm for 72 hours. Fifty ml of the shake flask broth from each of four separate shake flasks was used to inoculate a 3 liter fermentation vessel.

Fermentation batch medium was composed per liter of 250 g of glucose, 5 g of $(NH_4)_2SO_4$, 2.5 g of $KH_2PO_4$, 0.5 g of $CaCl_2.2H_2O$, 2 g of $MgSO_4.7H_2O$, 3 g of $K_2SO_4$, 1 g of citric acid, 1 ml of anti-foam, and 0.75 ml of trace metals solution. The trace metals solution was composed per liter of 13.8 g of $FeSO_4.7H_2O$, 14.3 g of $ZnSO_4.7H_2O$, 11.6 g of $MnSO_4.H_2O$, 2.5 g of $CuSO_4.5H_2O$, 0.5 g of $NiCl_2.6H_2O$, and 3.3 g of citric acid monohydrate. Fermentation feed medium was composed per kilogram of 406 g of maltose, 0.5 g of citric acid monohydrate, and 1 ml of anti-foam.

A total of 2 liters of the fermentation batch medium was added to an Applikon Biotechnology two liter glass jacketed fermentor (Applikon Biotechnology, Schiedam, Netherlands). Fermentation feed medium was dosed at a rate of 0 to 4 g/l/hr for a period of 185 hours. The fermentation vessel was maintained at a temperature of 34° C. and pH was controlled using an Applikon 1030 control system (Applikon Biotechnology, Schiedam, Netherlands) to a set-point of 5.1+/−0.1. Air was added to the vessel at a rate of 1 vvm and the broth was agitated by Rushton impeller rotating at 1100 rpm. At the end of the fermentation, whole broth was harvested from the vessel and centrifuged at 3000×g to remove the biomass. The supernatant was sterile filtered and stored at 5 to 10° C.

Example 9

Purification of *Humicola insolens* GH62A Polypeptide Having Alpha-L-Arabinofuranosidase Activity Fermentation broth supernatant (Example 8) containing recombinant *Humicola insolens* GH62A polypeptide having alpha-L-arabinofuranosidase activity expressed in *Aspergillus niger* was first buffer-exchanged into 25 mM sodium acetate pH 5.1 by passing through 400 ml of SEPHADEX™ G-25 fine resin (GE Healthcare, Piscataway, N.J., USA) equilibrated in the same buffer. The resulting buffer-exchanged material (50 ml) was then purified using a MONO S™ HR 16/10 column (GE Healthcare, Piscataway, N.J., USA) equilibrated with the same buffer, and then eluted with a linear gradient of 0-0.5 M sodium chloride. Next, fractions showing UV absorbance at 280 nm were analyzed by SDS-PAGE. A 2.5 μl fraction aliquot was separated on a CRITERION® 8-16% Tris-HCl SDS-PAGE gel according to the manufacturer's suggested conditions. PRECISION PLUS PROTEIN™ standards were used as molecular weight markers. The gel was removed from the cassette and stained with INSTANTBLUE™ Coomassie Blue protein stain (Expedeon Protein Solutions, Cambridge, UK) according to the manufacturer's suggested conditions. Fractions showing UV absorbance at 280 nm were also assayed for activity with medium viscosity wheat arabinoxylan (Megazyme International Ireland, Ltd., Bray, Co. Wicklow, Ireland). Fractions were diluted and incubated in a 96-well COSTAR® microtiter plate (Corning Inc., Corning, N.Y., USA) with 4.75 mg of wheat arabinoxylan per ml of 50 mM sodium acetate pH 5 with 0.01% (w/v) TWEEN® 20 in a total volume of 200 μl for 70 minutes at 40° C. The reaction was stopped by addition of 50 μl of 2% sodium hydroxide, and the reducing sugar content determined using a para-hydroxybenzoic acid hydrazide (PHBAH, Sigma, St. Louis, Mo., USA) assay adapted to a 96 well microplate format as described below. Briefly, a 100 μl aliquot of sample was placed in a 96 well conical bottom COSTAR® microtiter plate. Reactions were initiated by adding 50 μl of 1.5% (w/v) PHBAH in 2% NaOH to each well. Plates were heated uncovered at 95° C. for 10 minutes. Plates were allowed to cool to room temperature and 50 μl of $H_2O$ added to each well. A 100 μl aliquot from each well was transferred to a flat bottom 96 well plate and the absorbance at 410 nm was measured using a SPECTRAMAX® Microplate Reader (Molecular Devices, Sunnyvale, Calif., USA). Glucose standards (0.100-0.065 mg/ml) were used to prepare a standard curve to convert the obtained absorbance values at 410 nm into glucose equivalents, and quantify the amount of reducing sugars released in the assay. Fractions containing a long, diffuse band on SDS-PAGE from 40-150 kD, and also having activity with wheat arabinoxylan, were pooled, with a total volume of 48 ml.

The pooled material was next concentrated to a 1.5 ml volume using a VIVASPIN™ 20 ultrafiltration concentrator with a 10 kDa molecular weight cut-off membrane. The concentrated material was then purified using a HILOAD™ 26/60 SUPERDEX™ 75 Prep Grade column (GE Healthcare, Piscataway, N.J., USA) in 25 mM sodium acetate pH 5 with 125 mM sodium chloride. Column fractions were analyzed and pooled in a similar manner by SDS-PAGE and wheat arabinoxylan activity as described above, to yield purified *Humicola insolens* alpha-L-arabinofuranosidase. Protein concentration of the purified *Humicola insolens* alpha-L-arabinofuranosidase was determined using a Microplate BCA™ Protein Assay Kit (Pierce, Rockford, Ill., USA).

Example 10

Enzyme Activity of the *Humicola insolens* GH62A Polypeptide Having alpha-L-arabinofuranosidase Activity Purified *Humicola insolens* GH62A polypeptide having alpha-L-arabinofuranosidase activity (Example 9) was diluted and incubated in a 96-well COSTAR® microtiter plate with 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. After incubation, the plate was cooled on ice, and then the reactions were filtered through ULTRAFREE®-0.5 centrifugal filters with BIOMAX® 5 kDa molecular weight cut-off membranes (Millipore, Billerica, Mass., USA). The filtrates were then analyzed for sugar content.

Sugar concentrations of sample filtrates were measured after elution by 0.005 M sulfuric acid with 0.05% w/w benzoic acid at a flow rate of 0.6 ml per minute from a 4.6×250 mm AMINEX® HPX-87H column (Bio-Rad Laboratories, Inc., Hercules, Calif., USA) at 65° C. with quantitation by integration of glucose, arabinose, and xylose signals from refractive index detector (CHEMSTATION®, AGILENT® 1100 HPLC, Agilent Technologies, Santa Clara, Calif., USA) calibrated by pure sugar samples. The *Humicola insolens* polypeptide having alpha-L-arabinofuranosidase activity was observed to release 92.6 mg of arabinose/mg enzyme protein and 7.4 mg of xylose/mg enzyme protein from wheat arabinoxylan under the assay conditions.

Deposit of Biological Material

The following biological material has been deposited under the terms of the Budapest Treaty with the Agricultural Research Service Patent Culture Collection (NRRL), Northern Regional Research Center, 1815 University Street, Peoria, Ill., 61604, USA, and given the following accession number:

| Deposit | Accession Number | Date of Deposit |
|---|---|---|
| E. coli pHinsGH62A | NRRL B-50075 | Nov. 20, 2007 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated polynucleotide encoding a polypeptide having alpha-L-arabinofuranosidase activity, selected from the group consisting of:

(a) a polynucleotide encoding a polypeptide comprising an amino acid sequence having at least 95% sequence identity to the mature polypeptide of SEQ ID NO: 2;

(b) a polynucleotide that hybridizes under at least high stringency conditions with the mature polypeptide coding sequence of SEQ ID NO: 1 or the cDNA sequence thereof, or the full-length complementary strand thereof, wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.; and (c) a polynucleotide comprising a nucleotide sequence having at least 95% sequence identity to the mature polypeptide coding sequence of SEQ ID NO: 1 or the cDNA sequence thereof.

2. The polynucleotide of claim 1, wherein the polypeptide comprises an amino acid sequence having 96%, 97%, 98%, or 99% sequence identity to the mature polypeptide of SEQ ID NO: 2.

3. The polynucleotide of claim 2, wherein the polypeptide comprises or consists of SEQ ID NO: 2 or the mature polypeptide thereof, or a fragment thereof having alpha-L-arabinofuranosidase activity.

4. The polynucleotide of claim 1, which hybridizes under very high stringency conditions with the mature polypeptide coding sequence of SEQ ID NO: 1 or the cDNA sequence thereof, or the full-length complementary strand thereof, wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.

5. The polynucleotide of claim 1, which comprises a nucleotide sequence having 96%, 97%, 98%, or 99% sequence identity to the mature polypeptide coding sequence of SEQ ID NO: 1 or the cDNA sequence thereof.

6. The polynucleotide of claim 5, which comprises or consists of SEQ ID NO: 1 or the mature polypeptide coding sequence thereof, or a subsequence thereof encoding a fragment having alpha-L-arabinofuranosidase activity.

7. The polynucleotide of claim 1, which is contained in plasmid pHinsGH62A which is contained in *E. coli* NRRL B-50075.

8. A nucleic acid construct comprising the polynucleotide of claim 1 operably linked to one or more (several) control sequences that direct the production of the polypeptide having alpha-L-arabinofuranosidase activity in an expression host.

9. A recombinant expression vector comprising the nucleic acid construct of claim 8.

10. A recombinant host cell comprising the nucleic acid construct of claim 8.

11. A method of producing a polypeptide having alpha-L-arabinofuranosidase activity, comprising: (a) cultivating the host cell of claim 10 under conditions conducive for production of the polypeptide; and (b) recovering the polypeptide.

12. A transgenic plant, plant part or plant cell transformed with the polynucleotide of claim 1.

13. A method of producing a polypeptide having alpha-L-arabinofuranosidase activity, comprising: (a) cultivating the transgenic plant or plant cell of claim 12 under conditions conducive for production of the polypeptide; and (b) recovering the polypeptide.

* * * * *